US00RE47104E

(19) United States
(12) Reissued Patent
Furno et al.

(10) Patent Number: US RE47,104 E
(45) Date of Reissued Patent: Oct. 30, 2018

(54) SUPERABSORBENT COMPOSITION WITH TANNINS FOR ODOR CONTROL

(71) Applicant: EVONIK DEGUSSA GMBH, Essen (DE)

(72) Inventors: Franck Furno, Clementi (SG); Laurent Wattebled, Düsseldorf (DE); Anne Ix-Mund, Kerken (DE); Harald Schmidt, Müheim an der Ruhr (DE); Markus Henn, Gelsenkirchen (DE); Jörg Harren, Baesweiler (DE)

(73) Assignee: Evonik Degussa GmbH, Essen (DE)

(21) Appl. No.: 15/049,561

(22) Filed: Feb. 22, 2016

Related U.S. Patent Documents

Reissue of:
(64) Patent No.: 8,658,146
Issued: Feb. 25, 2014
Appl. No.: 12/679,631
Filed: May 7, 2010

(30) Foreign Application Priority Data

Sep. 24, 2007 (DE) ..... 10 2007 045 724

(51) Int. Cl.

| | |
|---|---|
| ***A01N 65/08*** | (2009.01) |
| ***A61K 31/78*** | (2006.01) |
| ***C08F 220/06*** | (2006.01) |
| ***A61L 15/60*** | (2006.01) |
| ***A61L 15/46*** | (2006.01) |
| ***C08J 3/12*** | (2006.01) |
| ***C08J 3/24*** | (2006.01) |
| *C08F 220/40* | (2006.01) |

(52) U.S. Cl.
CPC ..... *C08F 220/06* (2013.01); *A61L 15/46* (2013.01); *A61L 15/60* (2013.01); *C08J 3/128* (2013.01); *C08J 3/245* (2013.01); *A61L 2300/216* (2013.01); *A61L 2300/30* (2013.01); *A61L 2300/622* (2013.01); *C08F 220/40* (2013.01); *C08J 2300/14* (2013.01); *C08J 2333/02* (2013.01)

(58) Field of Classification Search
CPC ..... C08F 220/06
USPC ..... 424/76.6
See application file for complete search history.

(56) References Cited

U.S. PATENT DOCUMENTS

| | | | | |
|---|---|---|---|---|
| 3,903,259 | A | 9/1975 | Hart | |
| 4,076,663 | A | 2/1978 | Masuda et al. | |
| 4,131,576 | A | 12/1978 | Iovine et al. | |
| 4,172,123 | A | 10/1979 | Smart et al. | |
| 4,179,367 | A | 12/1979 | Barthell et al. | |
| 4,286,082 | A | 8/1981 | Tsubakimoto et al. | |
| 4,340,706 | A | 7/1982 | Obayashi et al. | |
| 4,356,190 | A | 10/1982 | Kraskin | |
| 4,465,017 | A | 8/1984 | Simmons | |
| 4,587,308 | A | 5/1986 | Makita et al. | |
| 4,766,173 | A | 8/1988 | Bailey et al. | |
| 4,812,486 | A | 3/1989 | Hosokawa et al. | |
| 4,857,610 | A | 8/1989 | Chmelir et al. | |
| 4,893,999 | A | 1/1990 | Chmelir et al. | |
| 5,045,322 | A | 9/1991 | Blake et al. | |
| 5,159,069 | A * | 10/1992 | Hirayama et al. | 536/118 |
| 5,385,983 | A | 1/1995 | Graham | |
| 5,409,771 | A | 4/1995 | Dahmen et al. | |
| 5,447,727 | A | 9/1995 | Graham | |
| 5,595,731 | A | 1/1997 | Vallieres | |
| 5,610,220 | A | 3/1997 | Klimmek et al. | |
| 5,624,967 | A | 4/1997 | Hitomi et al. | |
| 5,672,633 | A | 9/1997 | Brehm et al. | |
| 5,712,316 | A | 1/1998 | Dahmen et al. | |
| 5,773,542 | A | 6/1998 | Koudate et al. | |
| 5,986,042 | A | 11/1999 | Irizato et al. | |
| 6,060,557 | A | 5/2000 | Dahmen et al. | |
| 6,156,334 | A | 12/2000 | Meyer-Ingold et al. | |
| 6,313,231 | B1 | 11/2001 | Hosokawa et al. | |
| 6,403,700 | B1 | 6/2002 | Dahmen et al. | |
| 6,403,900 | B2 | 6/2002 | Dahmen et al. | |
| 6,448,320 | B1 | 9/2002 | Igarashi et al. | |
| 6,469,080 | B2 | 10/2002 | Miyake et al. | |
| 6,599,989 | B2 | 7/2003 | Wada et al. | |
| 6,605,673 | B1 | 8/2003 | Mertens et al. | |
| 6,620,889 | B1 | 9/2003 | Mertens et al. | |
| 6,623,848 | B2 | 9/2003 | Brehm et al. | |
| 6,703,451 | B2 | 3/2004 | Hosokawa et al. | |
| 6,831,142 | B2 | 12/2004 | Mertens et al. | |
| 6,869,681 | B2 * | 3/2005 | Okamoto et al. | 428/373 |

(Continued)

FOREIGN PATENT DOCUMENTS

| | | |
|---|---|---|
| CN | 1281687 C | 10/2006 |
| DE | 2612846 | 2/1978 |

(Continued)

OTHER PUBLICATIONS

English translation of International Preliminary Report on Patentability completed on Aug. 7, 2008 in PCT/EP2006/011055.

(Continued)

*Primary Examiner* — Timothy J. Kugel
(74) *Attorney, Agent, or Firm* — Bernard Lau; Linda S. Li; Jason S. Ngui

(57) ABSTRACT

The present invention relates to a water-absorbing composition comprising water-absorbing polymer structures, on the surface of which is at least one tannin fraction which has a number-average molecular weight, determined in accordance with the test method described herein, of at least 1,000 g/mol, which has a weight-average molecular weight, determined in accordance with the test method described herein, of at least 1,000 g/mol, or which is a hydrolysable gallotannin.

The present invention also relates to a process for the preparation of a water-absorbing composition, the water-absorbing composition obtainable by this process, a composite, a process for the production of a composite, the composite obtainable by this process, chemical products, such as, for example, hygiene articles, the use of a water-absorbing composition or of a composite and the use of a tannin fraction.

7 Claims, 2 Drawing Sheets

(56) References Cited

U.S. PATENT DOCUMENTS 6,911,572 B1 6/2005 Bruhn et al.
6,916,465 B2 7/2005 Panzer et al.
6,958,429 B2 10/2005 Bruhn et al.
6,960,655 B2 11/2005 Cintio et al.
6,964,998 B2 11/2005 Wada et al.
6,998,367 B2 2/2006 Qin
7,144,957 B2 12/2006 Funk et al.
7,179,862 B2 2/2007 Mertens et al.
7,226,584 B2 6/2007 Lersch et al.
7,285,599 B2 10/2007 Mertens et al.
7,378,453 B2 5/2008 Nogi et al.
7,420,018 B2 9/2008 Wada et al.
7,473,470 B2 1/2009 Ishizaki et al.
7,510,988 B2 3/2009 Wada et al.
7,541,395 B2 6/2009 Reimann et al.
7,572,864 B2 8/2009 Mertens et al.
7,625,957 B2 12/2009 Harren et al.
7,728,079 B2 6/2010 Harren et al.
7,737,231 B2 6/2010 Handa et al.
7,825,169 B2 11/2010 Wada et al.
7,834,233 B2 11/2010 Cohen
7,868,075 B2 1/2011 Taniguchi et al.
7,999,147 B2 8/2011 Cohen
8,026,294 B2 9/2011 Wada et al.
8,148,485 B2 4/2012 Nogi et al.
8,349,913 B2 1/2013 Harren et al.
2002/0018802 A1 2/2002 Meyer-Ingold et al.
2002/0197257 A1 12/2002 Meyer-Ingold et al.
2003/0031588 A1* 2/2003 Schur ..... 422/28
2003/0135172 A1 7/2003 Whitmore et al.
2003/0207997 A1 11/2003 Mertens et al.
2003/0220211 A1 11/2003 Stoddart et al.
2004/0024374 A1 2/2004 Hjorth et al.
2004/0033961 A1* 2/2004 Gremminger et al. ..... A61K 31/4402 514/23
2004/0048955 A1* 3/2004 Wada et al. ..... A61F 13/8405 524/9
2005/0123591 A1 6/2005 Meyer-Ingold et al.
2005/0171235 A1 8/2005 Harren et al.
2006/0029567 A1 2/2006 Dutkiewicz
2006/0029782 A1 2/2006 Harren et al.
2006/0030828 A1 2/2006 Wilhelm et al.
2006/0057389 A1 3/2006 Reimann et al.
2006/0167178 A1* 7/2006 Kitamura et al. ..... 524/833
2007/0015860 A1 1/2007 Frank
2007/0066167 A1 3/2007 Wada et al.
2007/0066754 A1 3/2007 Loeker et al.
2007/0111004 A1 5/2007 Handa et al.
2007/0129495 A1 6/2007 Mertens et al.
2007/0225160 A1* 9/2007 Kitano et al. ..... 502/402
2007/0225422 A1* 9/2007 Sakamoto ..... C08F 2/44 524/458
2007/0260357 A1 11/2007 Issberner et al.
2008/0161512 A1 7/2008 Kawano et al.
2008/0221277 A1 9/2008 Walden et al.
2008/0280128 A1 11/2008 Furno et al.
2009/0023006 A1 1/2009 Bub et al.
2009/0105389 A1 4/2009 Walden et al.
2009/0130040 A1 5/2009 Jonchiere
2009/0134357 A1 5/2009 Bub et al.
2009/0202805 A1 8/2009 Furno et al.
2009/0209683 A1 8/2009 Reimann et al.
2009/0227741 A1 9/2009 Walden et al.
2009/0234314 A1 9/2009 Nakamura et al.
2009/0239995 A1 9/2009 Bub et al.
2010/0035757 A1 2/2010 Furno et al.
2010/0036004 A1 2/2010 Harren et al.
2010/0057027 A1 3/2010 Furno et al.
2010/0072421 A1 3/2010 Kitano et al.
2010/0099799 A1 4/2010 Fricker et al.
2010/0105808 A1 4/2010 Fricker et al.
2010/0105809 A1 4/2010 Fricker et al.
2010/0119830 A1 5/2010 Braig et al.
2010/0120940 A1 5/2010 Adachi et al.
2010/0222758 A1 9/2010 Dairoku et al.
2010/0292078 A1 11/2010 Braig et al.
2011/0034603 A1 2/2011 Fujino et al.
2011/0068300 A1 3/2011 Taniguchi et al.
2012/0083411 A1 4/2012 Ahmed et al.

FOREIGN PATENT DOCUMENTS

DE 2612846 A1 2/1978
DE 2706135 8/1978
DE 2706135 A1 8/1978
DE 2840010 6/1979
DE 2840010 A1 6/1979
DE 3503458 8/1985
DE 3503458 A1 8/1985
DE 3544770 A1 6/1987
DE 3713601 11/1988
DE 3713601 A1 11/1988
DE 3816252 A1 11/1988
DE 19909653 A1 9/1990
DE 4020780 C1 8/1991
DE 4323001 7/1993
DE 4244548 7/1994
DE 4244548 A1 7/1994
DE 4418818 1/1995
DE 4418818 A1 1/1995
DE 4333056 3/1995
DE 4333056 A1 3/1995
DE 19518645 C1 9/1996
DE 19529348 A1 2/1997
DE 3713601 A1 11/1998
DE 19825486 2/2000
DE 19825486 A1 2/2000
DE 19909653 A1 9/2000
DE 19909838 A1 9/2000
DE 19939662 A1 2/2001
DE 10160933 A1 6/2003
DE 10334271 2/2005
DE 10334271 A1 2/2005
DE 102005055497 5/2007
DE 102005055497 A1 5/2007
EP 0257951 A2 3/1988
EP 0532002 A1 3/1993
EP 0811390 A1 12/1997
EP 0811391 A1 12/1997
EP 0811392 A1 12/1997
EP 0889063 A1 1/1999
EP 1149595 A1 10/2001
EP 1358894 A1 11/2003
EP 1108745 B1 9/2005
EP 1598392 A2 11/2005
EP 0940148 B1 5/2006
EP 1795211 A2 6/2007
JP 56089838 7/1981
JP 60158861 1/1984
WO 199605234 A1 2/1996
WO 1996/031644 A1 10/1996
WO 1997046187 A1 12/1997
WO 1997046190 A1 12/1997
WO 1997046191 A1 12/1997
WO 199934843 A1 7/1999
WO 2000051651 A1 9/2000
WO 2000/071176 A1 11/2000
WO 2001030748 A1 5/2001
WO 2001/070191 A1 9/2001
WO 2001070210 A2 9/2001
WO 2001080914 A1 11/2001
WO 2002056812 A1 7/2002
WO 2003028778 A2 4/2003
WO 2004037903 A2 5/2004
WO 2005011860 2/2005
WO 2005011860 A2 2/2005
WO 2006020318 A2 2/2006
WO 2007057043 A1 5/2007
WO 2007057203 A2 5/2007

(56) References Cited

FOREIGN PATENT DOCUMENTS

| | | | |
|---|---|---|---|
| WO | 2007122343 | A1 | 11/2007 |
| WO | 2010052182 | A1 | 5/2010 |

OTHER PUBLICATIONS

F.L. Buchholz Modern Superabsorbent Polymer Technology, Chapter 1, "Absorbency and Superabsorbency," ©1998, Wiley-VCH, New York, pp. 1-17 (19 pages).
German language International Search Report dated Aug. 13, 2010 in PCT/EP2008/008081.
German language Written Opinion dated Aug. 13, 2010 in PCT/EP2008/008081.
German language Written Opinion dated Jun. 12, 2009 in PCT/EP2009/052347.
International Search Report dated Jun. 12, 2009 in PCT/EP2009/052347.
International Search Report dated Oct. 26, 2007 in PCT/EP2006/011055.
Mané (Assessment of the Molecular Weight Distribution of Tannin Fractions through MALDI-TOF MS Analysis of Protein-Tannin Complexes), 79 Anal. Chem. 2239 (2007) (10 pages).
Quercus lusitanica, web page, Wikipedia Online Encyclopedia, copyright Dec. 2011 (1 page).
Mane (Assessment of the Molecular Weight Distribution of Tannin Fractions through MALDI-TOF MS Analysis of Protein-Tannin Complexes, 79 Anal. Chem. 2239 (2007)).*
*Quercus lusitanica*, http://en.wikipedia.org/wiki/Quercus_lusitanica.*
International Preliminary Report on Patentability mailed on Aug. 16, 2010 in PCT/EP2006/011055.
Harren et al., U.S. Appl. No. 12/600,964, filed Dec. 15, 2009.

* cited by examiner

SUPERABSORBENT COMPOSITION WITH TANNINS FOR ODOR CONTROL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a national stage application under 35 U.S.C. 371 of international application No. PCT/EP2008/008081 filed Sep. 24, 2008, and claims priority to German Application No. DE 10 2007 045 724.5 filed Sep. 24, 2007, the disclosures of which are expressly incorporated herein by reference.

BACKGROUND

The present invention relates to water-absorbing compositions, a process for the preparation of a water-absorbing composition, the water-absorbing composition obtainable by this process, a composite, a process for the production of a composite, the composite obtainable by this process, chemical products, such as, for example, hygiene articles, the use of a water-absorbing composition or of a composite and the use of a tannin fraction.

Superabsorbers are water-insoluble crosslinked polymers which are capable of absorbing and retaining under pressure large amounts of aqueous liquids, in particular body fluids, preferably urine or blood, with swelling and formation of hydrogels. In general, these uptakes of liquid are an amount of water at least 10 times or even at least 100 times the dry weight of the superabsorber or superabsorbent compositions. Due to these characteristic properties, these polymers are mainly used in sanitary articles, such as baby nappies, incontinence products or sanitary towels. A comprehensive overview of superabsorbers and superabsorbent compositions, their use and their preparation is given by F. L. Buchholz and A. T. Graham (editors) in "Modern Superabsorbent Polymer Technology", Wiley-VCH, New York, 1998.

Superabsorbers are as a rule prepared by radical polymerization of usually partly neutralized monomers carrying acid groups in the presence of crosslinking agents. In this context, polymers having different absorber properties can be prepared by the choice of the monomer composition, the crosslinking agents as well as the polymerization conditions and the processing conditions for the hydrogel obtained after the polymerization. Further possibilities are offered by the preparation of graft polymers, for example using chemically modified starch, cellulose and polyvinyl alcohol in accordance with DE-OS 26 12 846.

DE 40 20 780 C1 discloses the after-treatment of superabsorbent polymers by post-crosslinking of the surfaces of the polymer particles. By the post-crosslinking of the surface of the water-absorbing polymer particles, the absorption capacity of the polymer particles under the action of pressures is increased in particular.

DE 199 09 653 A1 and DE 199 09 838 A1 describe pulverulent polymers which are post-crosslinked on the surface and absorb water, aqueous or serous liquids or blood, and which are based on monomers carrying acid groups and have been coated with a surface post-crosslinking agent and a cation in aqueous solution and post-crosslinked. The polymers disclosed in this prior art have advantageous absorption properties compared with conventional polymers, in particular a high permeability.

During more prolonged wearing of hygiene articles containing absorbent polymers, especially if these have already absorbed in part body fluids, such as urine, an unpleasant odor nuisance may immediately occur due to the organic constituents of the urine and the body heat of the person wearing the article. To counteract this, numerous attempts have been made to achieve binding of the odor-forming substances by appropriate admixtures in the constituents of the hygiene article other than the superabsorber or to cover up the odor by perfumes or the like. The introduction of such substances in the form of constituents other than superabsorbers often has a negative effect on the performance of these hygiene articles during wearing. Thus, the odor-inhibiting or odor-reducing substances which are initially present spatially separated from the superabsorber region are often introduced by the body fluids, for example by washing in, into the superabsorber-containing region of a hygiene article, where they then have a negative effect on the performance of the superabsorber and therefore of the hygiene article overall. A further disadvantage of this concept is that the majority of the body fluid released into the hygiene article is in any case in the superabsorber, and the odor-inhibiting or odor-reducing substances outside the superabsorber can display their action less well.

DE 198 25 486 and DE 199 39 662 A1 disclose the combination of superabsorbers with cyclodextrin for reducing odor. However, its is to be seen from this entirely promising approach that the cyclodextrin shows its odor-inhibiting action in the superabsorber only under certain conditions, namely when it is ensured that the cyclodextrin does not separate again from the superabsorber. It is preferable here for the cyclodextrin to be incorporated at least into the surface of the superabsorber article by the cyclodextrin and/or cyclodextrin derivatives being covalently and/or ionically bonded and/or enclosed therein.

DE 103 34 271 furthermore discloses superabsorber agglomerates which can contain a large number of odor-binding substances homogeneously in the agglomerate. However, this specification, which discloses an outstanding solution for the use of superabsorber fine particles, provides no superabsorbers having odor-binding properties which are particularly suitable for use in hygiene articles. Thus, in addition to an efficient and effective use of the odor-binding substances, the superabsorber properties influenced by these odor-binding substances are still in need of improvement.

DE-A-10 2005 055 497 teaches that superabsorbent polymers are provided with improved odor-binding properties by bringing them into contact with metal salts of ricinoleic acid and/or with amino acids.

In general, the present invention was based on the object of moderating or even overcoming the disadvantages emerging from the prior art.

SUMMARY

The present invention includes various embodiments as set forth herein.

One object according to the invention was to provide a water-absorbing composition which on the one hand has good odor-binding properties. In this context, on the other hand it is to be ensured that the performance of the hygiene article which contains this odor-binding superabsorber composition is essentially equally as good as or even better than the performance of the hygiene article with a superabsorber which does not contain the odor-binding substance like the odor-binding superabsorbent composition. In particular, the performance properties of the water-absorbing composition itself should as far as possible not be influenced at all or should at best be influenced little by the use of odor-binding additives, which are to be employed in the lowest possible amounts. The performance properties of the water-absorbing composition should advantageously even be improved by the addition of the odor-binding additive.

Furthermore the water-absorbing composition should, upon contact with aqueous body liquids, especially with urine or iron containing liquids, such as, for example, blood or menstruation liquid, not tend to become discolored, if possible.

An object according to the invention was furthermore to provide a process with which such a water-absorbing composition can be obtained.

An object according to the invention was moreover to provide a hygiene article which, in addition to good odor-binding properties, also shows a good performance.

The present invention was additionally based on the object of providing water-absorbing compositions which can generally be incorporated into composites or can also be used as a composite or as such in chemical products or constituents thereof.

FIGURES

The foregoing and other features, aspects, and advantages of the present invention will become better understood with regard to the following description, appended claims, and accompanying drawings where:

DETAILED DESCRIPTION

Figure 1:
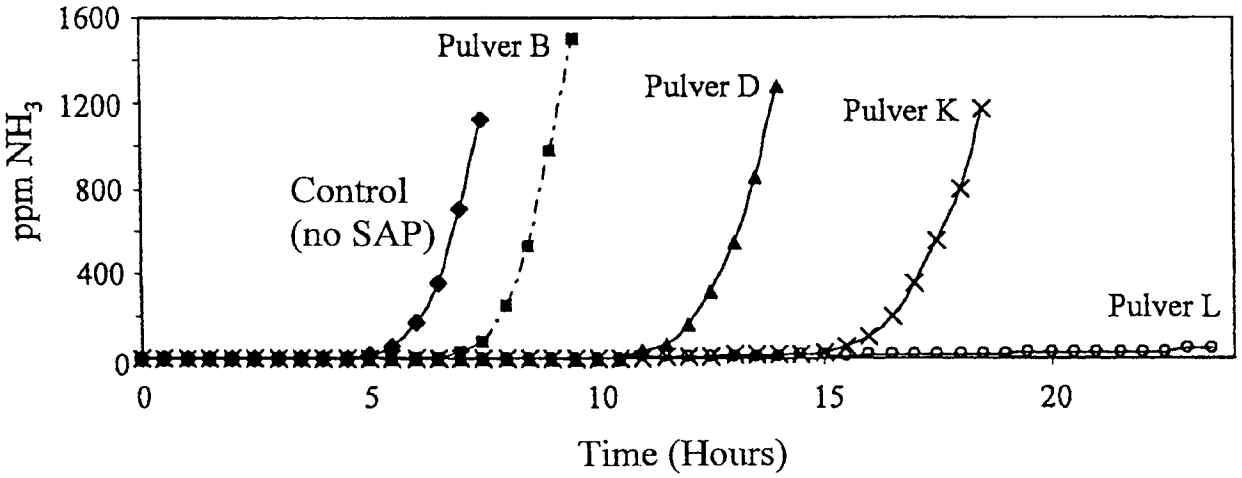
FIG. 1 is a graph showing a comparison of ppm of $NH_3$ and time in hours.

A contribution towards achieving the abovementioned objects is made by a water-absorbing composition comprising water-absorbing polymer structures, on the surface of which is at least one tannin fraction which has a number-average molecular weight, determined in accordance with the test method described herein, of at least 1,000 g/mol, still more preferably of at least 1,100 g/mol and most preferably of at least 1,200 g/mol, wherein preferably a number-average molecular weight of 10,000 g/mol, particularly preferably of 5,000 g/mol is not exceeded. For example, the number-average molecular weight is in a range of from 1,250 to 1,500 g/mol. In this connection, it is advantageous in particular if the tannin fraction has a polydispersity, determined in accordance with the test method described herein and defined as $M_w/M_n$, wherein $M_w$ is the weight-average molecular weight and $M_n$ is the number-average molecular weight, of less than 5, particularly preferably of less than 4 and most preferably of less than 3.

A contribution towards achieving the abovementioned objects is also made by a water-absorbing composition comprising water-absorbing polymer structures, on the surface of which is at least one tannin fraction which has a weight-average molecular weight, determined in accordance with the test method described herein, of at least 1,000 g/mol, still more preferably of at least 1,100 g/mol and most preferably of at least 1,200 g/mol, wherein preferably a weight-average molecular weight of 10,000 g/mol, particularly preferably of 5,000 g/mol is not exceeded. For example, the weight-average molecular weight is in a range of from 1,250 to 1,500 g/mol. In this case also, it is advantageous in particular if the tannin fraction has a polydispersity, determined in accordance with the test method described herein, of less than 5, particularly preferably of less than 4 and most preferably of less than 3.

A "tannin" in the context of the present invention is in general understood as meaning naturally occurring polyphenols. In principle, so-called "condensed tannins" or also "hydrolysable tannins" can be employed according to the invention, the use of hydrolysable tannins being particularly preferred and the use of hydrolysable gallotannins being most preferred.

In this connection, a further contribution towards achieving the abovementioned objects is therefore made quite generally by a water-absorbing composition comprising water-absorbing polymer structures, on the surface of which is at least one tannin fraction comprising hydrolysable gallotannins.

"Condensed tannins" are preferably understood as meaning tannins which are oligomers or polymers of flavonoid units which are linked to one another via C—C bonds. Such condensed tannins conventionally include 2 to 50 flavonoid units, but can also consist of more than 50 flavonoid units. Possible flavonoid units in this context are, in particular, catechol and epicatechol.

"Hydrolysable tannins" are preferably understood as meaning tannins which comprise a polyol, for example a carbohydrate, as the core, wherein gallic acid is bonded to the OH groups of this core molecule via ester bonds. Such hydrolysable tannins based on gallic acid are therefore often also called "gallotannins" In addition to gallic acid, however, the hydrolysable tannins can also be based on ellagic acid. Such hydrolysable tannins are often also called "ellagitannins" An excellent overview of tannins, in particular also of hydrolysable tannins and characterization thereof, is offered by the overview "Tannin Chemistry" by the author-ess Ann E Hagermann.

In this connection, tannins which are particularly preferred are those which are derived from the base skeleton of the following structure I (β-1,2,3,4,6-pentagalloyl-O-D-glucose)

structure I

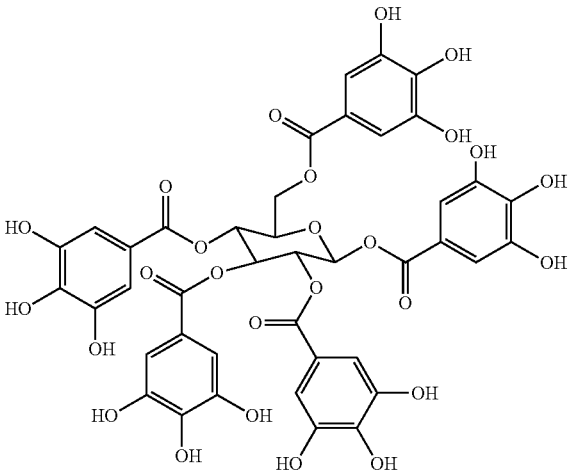

wherein to at least one of the OH groups of at least one of the gallic acid molecules bonded to the carbohydrate core (=gallic acid molecule of the first level, bonded as galloyl ester), preferably to one of the OH groups in the meta or para position, but preferably to at least one of the OH groups of 2, 3, 4 or 5 of the gallic acid molecules bonded to the carbohydrate core, there is bonded at least one further gallic acid molecule (=gallic acid molecule of the second level) via an ester bond (digalloyl ester). In this connection, it is particularly preferable for the tannin to be a tannin which is derived from the base skeleton of structure I and which includes at least one, preferably two, three, four or five gallic acid molecules of the second level. In particular, however, in this connection it is preferable for preferably at least 30 wt. %, particularly preferably at least 50 wt. %, still more preferably at least 75 wt. % and most preferably at least 95 wt. % of the tannins contained in the water-absorbing composition to have a molecular weight of more than 940 g/mol, particularly preferably more than 1,100 g/mol and moreover preferably more than 1,200 g/mol, here also preferably a molecular weight of 10,000 g/mol, particularly preferably of 5,000 g/mol not being exceeded. In order to establish whether a given tannin contains the abovementioned amounts of tannins having a molecular weight of more than 940 g/mol, it may be appropriate, for example, to subject the corresponding tannin to an HPLC analysis and to compare the elugram obtained in this context with the elugram of pure β-1,2,3,4,6-pentagalloyl-O-D-glucose. Such a method for determination of the molecular weight of gallotannins is described in the method part of the description. Besides β-1,2,3,4,6-pentagalloyll-O-D-glucose 2-6-di-O-galloyl-1,5-anhyhdro-D-glucitol (also called "Aceritannin"), Eugeniin, Casuricitin, Corilagin, Geraniin, Davidiin, Casuariin, Casuarinin, Castalagin, Castlin, Stachyurin, Vescalagin, Vescalin, Euphorbin A, Oenothein B, Woodfordin C, Cuphiin $D_1$ and Eugeniflorin $D_1$ shall be mentioned as further suitable tannins.

Furthermore tannins can be used in which one or more free hydroxyl groups are substituted by phosphate groups, such as it is for example the case in the product Floctan®4 from the company S. A. Ajinomoto OmniChem n. V., Belgium.

The use of hydrolysable gallotannins having the abovementioned weight-average or number-average molecular weights, in particular also with the abovementioned polydispersities, is particularly preferred according to the invention. According to a particular embodiment of the composition according to the invention, it is furthermore preferable for the total of all the tannins contained in the water-absorbing composition according to the invention to have the abovementioned weight-average or the abovementioned number-average molecular weight.

In principle, the tannins contained in the composition according to the invention, preferably the hydrolysable gallotannins contained in the composition according to the invention, can be isolated from the most diverse plant sources or optionally also obtained in the already purified form from commercial suppliers. The isolation of tannins from plant extracts, in particular also the isolation of hydrolysable tannins, is known to the person skilled in the art, for example, from the abovementioned overview by Ann E. Hagermann or from Salminen et al., "Distribution of Hydrolysable Tannins in the Foliage of Finnish Birch Species", Zeitschrift für Naturforschung, vol. 57c, pages 248-256 (2002). Examples which may be mentioned of suitable sources of tannins which can be employed according to the invention, in particular of hydrolysable tannins which can be employed according to the invention, are, in particular, plant extracts chosen from the group consisting of Rhus semialata extract, Rhus coriaria extract, Quercus infectoria extract, Quercus aegilops extract, Caesalpina spinosa extract, Caesalpina d. gyna extract, Valonea extract, such as Quercus Valonea extract or Quercus Macrolepsis extract, chestnut wood extract, such as Castanea Savita extract, and Terminalia chebula extract or mixtures of at least two of these, plant extracts from Rhus semialata and from Quercus infectoria being preferred and plant extracts from Rhus semialata being particularly preferred.

Where appropriate, the tannins obtained from plant sources, in particular the hydrolysable tannins obtained from plant sources, are to be worked up by suitable separation processes, for example by chromatography separation processes, such that tannin fractions are obtained which have the abovementioned values for the preferred number-average or for the preferred weight-average molecular weight.

In addition to isolation of the tannin fraction which can be employed according to the invention from plant sources, suitable tannin fractions can also be acquired from commercial suppliers. Possible fractions here are, besides the previously mentioned product Floctan® 4, for example, also the products Tanal O2C, Floctan® 1 or Brewtan® from S. A. Ajinomoto OmniChem n. V., Belgium.

According to a particularly preferred embodiment of the composition according to the invention, it is furthermore preferable for the at least one tannin fraction to be at least partly in the form of particles on the surface of the water-absorbing polymer structure, it being preferable in particular for at least 30 wt. %, particularly preferably at least 50 wt. %, still more preferably at least 75 wt. %, moreover preferably at least 95 wt. % and most preferably 100 wt. % of the particles of the at least one tannin fraction to have a size in a range of from 10 nm to 300 μm, particularly preferably 50 nm to 50 μm and most preferably 100 nm to 10 μm.

It is also preferable according to the invention for the water-absorbing composition to comprise the tannin or the tannin fraction in an amount in a range of from 0.001 to 10 wt. %, particularly preferably in a range of from 0.1 to 5 wt. % and most preferably in an amount in a range of from 0.2 to 2 wt. %, each based on the total weight of the water-absorbing polymer structures. In connection with the color stability of the water-absorbing compositions after a contact with body liquids it is, however, especially advantageous if the water-absorbing composition contains the tannin or the tannin fraction in an amount of not more than 0.75 wt. %, particularly preferably not more than 0.5 wt. % and most preferably not more than 0.4 wt.-%, each based on the total weight of the water-absorbing polymer structures. According to a particular embodiment of the water-absorbing composition according to the present invention this water-absorbing composition contains the tannin or the tannin fraction in an amount of 0.2 to 0.4 wt.-%, based on the total weight of the water-absorbing polymer structures.

The particles of the tannin fraction can optionally be immobilized on the surface of the water-absorbing polymer structures via a binder, it being possible in principle for organic or inorganic binders to be employed as the binder. Possible binders in this context are, in particular, thermoplastic hot melt adhesives, hydrophilic, preferably water-soluble polymers or also water itself. Thermoplastic hot melt adhesives which can be employed in this context are in particular those particulate compounds such as are mentioned as thermoplastic adhesives in WO-A-2005/011860. Hydrophilic, preferably water-soluble polymers which can be employed are, in particular, polyvinyl alcohols, which can be obtained by partial or complete hydrolysis of polyvinyl acetate, or polyalkylene glycols, in particular polyethylene glycols having a molecular weight in a range of from 1,000 to 50,000 g/mol, particularly preferably in a range of from 1,500 to 25,000 g/mol and most preferably in a range of from 2,000 to 15,000 g/mol.

Furthermore, it has been proven to be advantageous that not only the previously mentioned tannin fraction, particular preferably the previously described hydrolysable tannins with the previously described properties, are present at the surface of the water-absorbing polymer structures contained in the water-absorbing composition according to the present invention, but in addition thereto also one or more complex formation agent. It has been shown that the combined use of hydrolysable tannins and complex formation agents not only further significantly improves the odor-binding properties, but in addition to this also significantly improves the color stability of the water-absorbing composition upon contact with body liquids. Also, the combined use of hydrolysable tannins and complex formation agents allows using the tannins in lower amounts, which additionally improves the color stability.

A contribution towards achieving the abovementioned objects is therefore also made by a water-absorbing composition comprising water-absorbing polymer structures, on the surface of which is one or more complex formation agent as well as at least one tannin fraction which has a number-average molecular weight, determined in accordance with the test method described herein, of at least 1,000 g/mol, still more preferably of at least 1,100 g/mol and most preferably of at least 1,200 g/mol, wherein preferably a number-average molecular weight of 10,000 g/mol, particularly preferably of 5,000 g/mol is not exceeded. For example, the number-average molecular weight is in a range of from 1,250 to 1,500 g/mol. In this connection, it is advantageous in particular if the tannin fraction has a polydispersity, determined in accordance with the test method described herein and defined as $M_w/M_n$, wherein $M_w$ is the weight-average molecular weight and $M_n$ is the number-average molecular weight, of less than 5, particularly preferably of less than 4 and most preferably of less than 3.

A contribution towards achieving the abovementioned objects is also made by a water-absorbing composition comprising water-absorbing polymer structures, on the surface of which is one or more complex formation agent as well as at least one tannin fraction which has a weight-average molecular weight, determined in accordance with the test method described herein, of at least 1,000 g/mol, still more preferably of at least 1,100 g/mol and most preferably of at least 1,200 g/mol, wherein preferably a weight-average molecular weight of 10,000 g/mol, particularly preferably of 5,000 g/mol is not exceeded. For example, the weight-average molecular weight is in a range of from 1,250 to 1,500 g/mol. In this case also, it is advantageous in particular if the tannin fraction has a polydispersity, determined in accordance with the test method described herein, of less than 5, particularly preferably of less than 4 and most preferably of less than 3.

A contribution towards achieving the abovementioned objects is also made by a water-absorbing composition comprising water-absorbing polymer structures, on the surface of which is one or more complex formation agent as well as at least one tannin fraction comprising hydrolysable gallotannins.

A contribution towards achieving the abovementioned objects is also made by a water-absorbing composition comprising water-absorbing polymer structures, on the surface of which is one or more complex formation agent as well as at least one tannin fraction comprising a tannin, wherein it is preferred that this tannin fraction is one of the above mentioned tannin fractions (a tannin fraction having a weight-average molecular weight, determined in accordance with the test method described herein, of at least 1,000 g/mol, a tannin fraction having a number-average molecular weight, determined in accordance with the test method described herein, of at least 1,000 g/mol or a tannin fraction comprising hydrolysable tannins), wherein in this case the tannin fraction can be contained in the absorbent composition according to the present invention in a purified form or in the form of a plant extract, particularly in the form of a tee extract.

"Complex forming agents" are preferably understood as compounds that comprise two or more functional groups that can coordinate to multivalent metal-cations. These functional groups are for example organic acid groups, amine- or imine groups or sulfonic acid groups. According to the present invention particular preferred complex formation agents are aminopolycarboxylic acids, which are aminocarboxylic acids with three or more carboxylic groups, and salts thereof. Among these aminopolycarboxylic acids diethylenetriamine pentaacetic acid, triethylenetetramine hexaacetic acid, cyclohexane-1,2-diaminetetraacetic acid, N-2-hydroxyethylenediamine triacetic acid, ethylene glycol diethylether diamine tetraacetic acid, ethylenediamine tetrapropionic acid, N-alkyl-N'-carboxymethylaspartic acid, N-alkenyl-N'-carboxymethylaspartic acid, S,S-ethylenediamine-N,N' disuccinic acid and the alkali metal salts, alkaline earth metal salts, ammonium salts and amine salts thereof are particularly preferred. Among those diethylenetriamine pentaacetic acid, N-2-hydroxyethylenediamine triacetic acid and S,S-ethylenediamine-N,N' disuccinic acid and their salts are particularly preferred and the pentasodium salt of diethylenetriamine pentaacetic acid is most preferred.

In connection with the above described complex forming agents it is furthermore preferred that the water-absorbing composition comprises the complex forming agent in an amount in the range from 0.001 to 5 wt.-%, particular preferably in an amount in the range from 0.01 to 1 wt.-% and most preferably in an amount in the range from 0.05 to 0.5 wt. %, based on the total weight of the water-absorbing polymer structure.

The water-absorbing polymer structures contained in the composition according to the invention are preferably based on partly neutralized, crosslinked polyacrylates.

In this context, water-absorbing polymer structures which are preferred according to the invention are, in particular, fibers, foams or particles, fibers and particles being particularly preferred and particles being most preferred.

Polymer fibers which are preferred according to the invention have dimensions such that they can be incorporated as yarns for textiles and also directly into textiles. It is preferable according to the invention for the polymer fibers to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Polymer particles which are preferred according to the invention have dimensions such that they have an average particles size according to ERT 420.2-02 in the range of from 10 to 3,000 μm, preferably 20 to 2,000 μm and particularly preferably 150 to 850 μm or 150 to 600 μm. In this context it is particularly preferable for the content of polymer partides having a particle size in a range of from 300 to 600 μm to be at least 30 wt. %, particularly preferably at least 40 wt. %, moreover preferably at least 50 wt. % and most preferably at least 75 wt. %, based on the total weight of the water-absorbing polymer particles. According to another embodiment of the water-absorbing polymer structures according to the invention, the content of polymer particles having a particle size in a range of from 150 to 850 μm is at least 50 wt. %, particularly preferably at least 75 wt. %, moreover preferably at least 90 wt. % and most preferably at least 95 wt. %, based on the total weight of the water-absorbing polymer particles.

In a preferred embodiment of the water-absorbing polymer structures according to the invention, these are based on (α1) 20-99.999 wt. %, preferably 55-98.99 wt. % and particularly preferably 70-98.79 wt. % of polymerized ethylenically unsaturated monomers carrying acid groups or salts thereof or polymerized ethylenically unsaturated monomers containing a protonated or quaternized nitrogen, or mixtures thereof, mixtures containing at least ethylenically unsaturated monomers containing acid groups, preferably acrylic acid, being particularly preferred, (α2) 0-80 wt. %, preferably 0-44.99 wt. % and particularly preferably 0.1-44.89 wt. % of polymerized monoethylenically unsaturated monomers which can be copolymerized with (α1), (α3) 0.001-5 wt. %, preferably 0.01-3 wt. % and particularly preferably 0.01-2.5 wt. % of one or more crosslinking agents, (α4) 0-30 wt. %, preferably 0-5 wt. % and particularly preferably 0.1-5 wt. % of a water-soluble polymer, (α5) 0-20 wt. %, preferably 2.5-15 wt. % and particularly preferably 5-10 wt. % of water, and (α6) 0-20 wt. %, preferably 0-10 wt. % and particularly preferably 0.1-8 wt. % of one or more auxiliaries, the sum of the amounts by weight of (α1) to (α6) being 100 wt. %.

The monoethylenically unsaturated monomers (α1) containing acid groups can be partly or completely, preferably partly neutralized. Preferably, the monoethylenically unsaturated monomers containing acid groups are neutralized to the extent of at least 25 mol %, particularly preferably to the extent of at least 50 mol % and moreover preferably to the extent of 50-80 mol %. According to particular embodiments of the composition according to the invention, however, this comprises water-absorbing polymer structures which are neutralized to the extent of at most 78 mol %, particularly preferably to the extent of at most 70 mol % and to the extent of at least 50 mol %. In this connection, according to one embodiment of the composition according to the invention, the degree of neutralization of the water-absorbing polymer structures can be in a range of from 65 to 80 mol %, particularly preferably in a range of from 70 to 78 mol %, and according to another embodiment in a range of from 45 to 65 mol %, particularly preferably in a range of from 50 to 60 mol %. Reference is furthermore made to DE 195 29 348 A1, the disclosure of which is introduced herewith as reference. The neutralization can also be carried out partly or completely after the polymerization. The neutralization can furthermore be carried out with alkali metal hydroxides, alkaline earth metal hydroxides, ammonia and carbonates and bicarbonates. In addition, any further base which forms a water-soluble salt with the acid is conceivable. A mixed neutralization with various bases is also conceivable. Neutralization with ammonia and alkali metal hydroxides is preferred, particularly preferably with sodium hydroxide and with ammonia.

Furthermore, the free acid groups can predominate in a polymer, so that this polymer has a pH in the acidic range. This acidic water-absorbing polymer can be at least partly neutralized by a polymer having free basic groups, preferably amine groups, which is basic compared with the acidic polymer. These polymers are called "mixed-bed ion exchange absorbent polymers" (MBIEA polymers) in the literature and are disclosed, inter alia, in WO 99/34843 A1. The disclosure of WO 99/34843 A1 is introduced herewith as reference and thus forms part of the disclosure. As a rule, MBIEA polymers are a composition which comprises on the one hand basic polymers which are capable of exchanging anions, and on the other hand a polymer which is acidic compared with the basic polymer and is capable of exchanging cations. The basic polymer contains basic groups and is typically obtained by polymerization of monomers which carry basic groups or groups which can be converted into basic groups. These monomers are above all those which contain primary, secondary or tertiary amines or the corresponding phosphines or at least two of the above functional groups. This group of monomers includes, in particular, ethyleneamine, allylamine, diallylamine, 4-aminobutene, alkyloxycyclins, vinylformamide, 5-aminopentene, carbodiimide, formaldacin, melamine and the like, and secondary or tertiary amine derivatives thereof.

Preferred ethylenically unsaturated monomers (α1) containing acid groups are preferably those compounds which are mentioned as ethylenically unsaturated monomers (α1) containing acid groups in WO 2004/037903 A2, which is introduced herewith as reference and thus forms part of the disclosure. Particularly preferred ethylenically unsaturated monomers (α1) containing acid groups are acrylic acid and methacrylic acid, acrylic acid being most preferred.

According to one embodiment of the process according to the invention, water-absorbing polymer structures in which the monoethylenically unsaturated monomers (α2) which can be copolymerized with (α1) are acrylamides, methacrylamides or vinylamides are employed.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino(meth)acrylamide, dimethyl(meth) acrylamide or diethyl (meth)acrylamide. Possible ylnylamides are, for example, N-vinylamides, N-vinylformamides, N-vinylacetamides, N-vinyl-N-methylacetamides, N-vinyl-N-methylformamides and vinylpyrrolidone. Among these monomers, acrylamide is particularly preferred.

According to another embodiment of the process according to the invention, water-absorbing polymer structures in which the monoethylenically unsaturated monomers (α2) which can be copolymerized with (α1) are water-soluble monomers are employed. In this connection, alkoxypolyalkylene oxide (meth)acrylates, such as methoxypolyethylene glycol (meth)acrylates, are preferred in particular.

Water-dispersible monomers are furthermore preferred as monoethylenically unsaturated monomers (α2) which can be copolymerized with (α1). Preferred water-dispersible monomers are acrylic acid esters and methacrylic acid esters, such as methyl (meth)acrylate, ethyl (meth)acrylate, propyl (meth) acrylate or butyl (meth)acrylate.

The monoethylenically unsaturated monomers (α2) which can be copolymerized with (α1) furthermore include methylpolyethylene glycol allyl ether, vinyl acetate, styrene and isobutylene.

Crosslinking agents (α3) which are preferably employed are those compounds which are mentioned as crosslinking agents (α3) in WO 2004/037903 A2. Among these crosslinking agents, water-soluble crosslinking agents are particularly preferred. In this context N,N'-methylenebisacrylamide, polyethylene glycol di(meth)acrylates, triallylmethylammonium chloride, tetraallylammonium chloride and allylnonaethylene glycol acrylate prepared with 9 mol of ethylene oxide per mol of acrylic acid are most preferred.

The polymer structures can comprise as water-soluble polymers (α4) water-soluble polymers such as partly or completely hydrolyzed polyvinyl alcohol, polyvinylpyrrolidone, starch or starch derivatives, polyglycols or polyacrylic acid, preferably in a polymerized-in form. The molecular weight of these polymers is not critical, as long as they are water-soluble. Preferred water-soluble polymers are starch or starch derivatives or polyvinyl alcohol. The water-soluble polymers, preferably synthetic polymers, such as polyvinyl alcohol, can also serve as a graft base for the monomers to be polymerized.

Auxiliaries (α6) which are contained in the polymer structures are, preferably, standardizing agents, odor-binding agents, surface-active agents or antioxidants and those additives which have been employed for the preparation of the polymer structures (initiators etc.).

In a particular embodiment of the polymer structures according to the invention, these are based to the extent of at least 50 wt. %, preferably to the extent of at least 70 wt. % and moreover preferably to the extent of at least 90 wt. % on monomers which carry carboxylate groups. It is furthermore preferable according to the invention for component (α1) to be neutralized to the extent of at least 50 wt. %, it being possible according to one embodiment of the process according to the invention for the degree of neutralization of the water-absorbing polymer structures to be in a range of from 65 to 80 mol %, particularly preferably in a range of from 70 to 78 mol % and according to another embodiment in a range of from 45 to 65 mol %, particularly preferably in a range of from 50 to 60 mol %.

According to a preferred embodiment of the composition according to the invention, it is furthermore preferable for the water-absorbing polymer structures to have an inner region and an outer region surrounding the inner region, the outer region having a higher degree of crosslinking than the inner region. Such an inhomogeneous degree of crosslinking can be achieved by the water-absorbing polymer structures being post-crosslinked by coating with a suitable surface post-crosslinking agent which contains at least two functional groups which can react with the functional groups in the outer region of the water-absorbing polymer structure.

A contribution towards achieving the abovementioned objects is also made by a process for the preparation of a water-absorbing composition comprising the process steps:

i) provision of a water-absorbing polymer structure;

ii) post-crosslinking of the water-absorbing polymer structure;

iii) bringing the water-absorbing polymer structure into contact
   - a) with at least one tannin fraction which has a number-average molecular weight, determined in accordance with the test method described herein, of at least 1,000 g/mol, or
   - b) with at least one tannin fraction which has a weight-average molecular weight, determined in accordance with the test method described herein, of at least 1,000 g/mol, or
   - c) with at least one tannin fraction comprising hydrolysable gallotannins;

wherein process step iii) can be carried out before, during or after process step ii), but is preferably carried out after process step ii) (which means that water-absorbing polymer structures which have already been post-crosslinked on the surface are brought into contact with the corresponding tannins).

Water-absorbing polymer structures are first provided in process step i) of the process according to the invention.

In this context, water-absorbing polymer structures provided in process step i) are preferably polymers which have been obtained by a process including the process steps:

a) radical polymerization of ethylenically unsaturated, optionally partly neutralized monomers carrying acid groups in the presence of a crosslinking agent to form a hydrogel;

b) optionally comminution of the hydrogel;

c) at least partial drying of the optionally comminuted hydrogel to give water-absorbing polymer structures;

d) optionally grinding of the absorbent polymer structure obtained in this way and sieving to a desired particle size fraction;

e) optionally further surface modifications of the water-absorbing polymer structures obtained in this way.

The free radical polymerization which is carried out in process step a) is preferably carried out in aqueous solution, where this aqueous solution preferably contains, in addition to water as the solvent, (α1) the ethylenically unsaturated monomers carrying acid groups or salts thereof, acrylic acid being particularly preferred as the monomer carrying acid groups, (α2) optionally monoethylenically unsaturated monomers which can be copolymerized with (α1), (α3) the crosslinking agent, (α4) optionally a water-soluble polymer, and (α6) optionally one or more auxiliaries.

Preferred monoethylenically unsaturated monomers which can be copolymerized with (α1), water-soluble polymers and auxiliaries are in turn those compounds which have already been mentioned above as monomers which can be copolymerized with (α1), as water-soluble polymers and as auxiliaries in connection with the water-absorbing polymer structures contained in the composition according to the invention.

The water-absorbing polymer structures can be prepared from the above-mentioned monomers, comonomers, crosslinking agents, water-soluble polymers and auxiliary substances by various polymerization methods. There may be mentioned by way of example in this connection bulk polymerization, which is preferably carried out in kneading reactors, such as extruders, solution polymerization, spray polymerization, inverse emulsion polymerization and inverse suspension polymerization.

The solution polymerization is preferably carried out in water as the solvent. The solution polymerization can be carried out continuously or discontinuously. A broad spectrum of possibilities of variation with respect to the reaction circumstances, such as temperatures, nature and amount of the initiators and also of the reaction solution, is to be found from the prior art. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are introduced herewith as reference and therefore form part of the disclosure.

The polymerization is initiated by an initiator as is generally conventional. Initiators which can be used for initiation of the polymerization are all the initiators which form free radicals under the polymerization conditions and are conventionally employed in the preparation of superabsorbers. Initiation of the polymerization by the action of electron beams on the polymerizable aqueous mixture is also possible. Nevertheless, the polymerization can also be initiated in the absence of initiators of the abovementioned type by the action of high-energy radiation in the presence of photoinitiators. Polymerization initiators can be contained in a solution of monomers according to the invention in dissolved or dispersed form. Possible initiators are all the compounds known to the person skilled in the art which dissociate into free radicals. These include, in particular, those initiators which have already been mentioned as possible initiators in WO 2004/037903 A2.

A redox system comprising hydrogen peroxide, sodium peroxodisulphate and ascorbic acid is particularly preferably employed for preparation of the water-absorbing polymer structures.

Inverse suspension and emulsion polymerization can also be used for preparation of the polymer structures. According to these processes an aqueous, partly neutralized solution of monomers ($\alpha 1$) and ($\alpha 2$), optionally containing water-soluble polymers and auxiliary substances, is dispersed in a hydrophobic organic solvent with the aid of protective colloids and/or emulsifiers and the polymerization is started by free radical initiators. The crosslinking agents either are dissolved in the monomer solution and are metered together with this, or are added separately and optionally during the polymerization. The addition of a water-soluble polymer ($\alpha 4$) as a graft base is optionally carried out via the monomer solution or by direct initial introduction into the oily phase. The water is then removed azeotropically from the mixture and the polymer is filtered off.

Both in the case of solution polymerization and in the case of inverse suspension and emulsion polymerization, the crosslinking can furthermore be carried out by polymerizing in the polyfunctional crosslinking agent dissolved in the monomer solution and/or by reaction of suitable crosslinking agents with functional groups of the polymer during the polymerization steps. The processes are described, for example, in the publications U.S. Pat. No. 4,340,706, DE 37 13 601, DE 28 40 010 and WO 96/05234 A1, the corresponding disclosure of which is introduced herewith as reference.

The hydrogels obtained in the solution polymerization or the inverse suspension and emulsion polymerization in process step a) are at least partly dried in process step c).

In the case of solution polymerization in particular, however, it is preferable for the hydrogels first to be comminuted in an additional process step b) before the drying. This comminution is carried out by comminution devices known to the person skilled in the art, such as, for example, a meat chopper.

Drying of the hydrogel is preferably carried out in suitable dryers or ovens. Rotary tube ovens, fluidized bed dryers, plate dryers, paddle dryers or infrared dryers may be mentioned by way of example. It is furthermore preferable according to the invention for the drying of the hydrogel in process step c) to be carried out down to a water content of from 0.5 to 50 wt. %, preferably from 1 to 25 wt. %, particularly preferably 2 to 10 wt. %, the drying temperatures conventionally being in a range of from 100 to 200° C.

The at least partly dried water-absorbing polymer structures obtained in process step c) can also be ground in a further process step d), especially if they have been obtained by solution polymerization, and sieved off to the abovementioned desired particle size. Grinding of the dried water-absorbing polymer structures is preferably carried out in suitable mechanical comminution devices, such as, for example, a ball mill.

After the drying of the hydrogels and the further making up of the dried water-absorbing polymer structures optionally carried out, these can be modified in the surface region in a further process step e) (the surface post-crosslinking according to process step ii) described in more detail in the following and the treatment with tannins in process step iii) are excluded from the surface modification carried out in process step e)).

The preferred modification measure to be mentioned here is the bringing into contact of the outer region of the polymer structures with a compound containing $Al^{3+}$ ions before, during or after, preferably after the surface post-crosslinking according to process step ii). In this context it is preferable for the compound containing $Al^{3+}$ ions to be brought into contact with the water-absorbing polymer structures in an amount in a range of from 0.01 to 30 wt. %, particularly preferably in an amount in a range of from 0.05 to 20 wt. % and moreover preferably in an amount in a range of from 0.1 to 5 wt. %, in each case based on the weight of the water-absorbing polymer structures.

The outer region of the water-absorbing polymer structures is preferably brought into contact with the compound containing $Al^{3+}$ ions by mixing the polymer structure with the compound under dry conditions, or by bringing the polymer structures into contact with a fluid $F_1$ comprising a solvent, preferably water, water-miscible organic solvents, such as, for example, methanol or ethanol, or mixtures of at least two of these, and the compound containing $Al^{3+}$ ions, the components being brought into contact preferably by spraying the polymer particles with the fluid $F_1$ and mixing. In this connection, it is furthermore preferable for the polymer structures to be brought into contact with the fluid $F_1$ comprising the compound containing $Al^{3+}$ ions in a two-stage process. In this context, the two-stage process includes a first mixing operation, in which a large number of polymer structures are mixed with the fluid $F_1$, and a second mixing operation, in which the fluid $F_1$ is homogenized inside the polymer structures, the polymer structures being mixed in the first mixing operation at a speed such that the kinetic energy of the individual polymer structures on average is greater than the adhesion energy between the individual polymer structures, and the polymer structures being mixed thoroughly in the second mixing operation at a lower speed than in the first mixing operation.

By the treatment of the polymer structures with the fluid $F_1$ comprising the compound containing $Al^{3+}$ ions by the two-stage process described above, polymer structures having improved absorption properties can be obtained.

In this context, the fluid $F_1$ preferably comprises the compound containing $Al^{3+}$ ions, without taking into account water of crystallization, in an amount in a range of from 0.1 to 50 wt. %, particularly preferably in an amount in a range of from 1 to 30 wt. %, in each case based on the total weight of the fluid $F_1$. It is furthermore preferable for the fluid $F_1$ to be brought into contact with the polymer structures in an amount in a range of from 0.01 to 15 wt. %, particularly preferably in an amount in a range of from 0.05 to 6 wt. %, in each case based on the weight of the polymer structures.

Preferred compounds containing $Al^{3+}$ ions are $AlCl_3 \times 6H_2O$, $NaAl(SO_4)_2 \times 12H_2O$, $KAl(SO_4)_2 \times 12H_2O$, $Al_2(SO_4)_3 \times 14\text{-}18H_2O$ or aluminum lactate.

A further surface modification measure which may be mentioned at this point is bringing the water-absorbing polymer structures into contact with inorganic particles, for example with finely divided silicon dioxide, which is preferably applied in aqueous suspension, or with silica sol.

The modification measures carried out above in process step e), in particular the treatment with a compound containing $Al^{3+}$ ions, can in principle also be carried out while process steps ii) and iii) are being carried out, after process steps ii) and iii) have been carried out, after process step ii) has been carried out but before process step iii) has been carried out or after process step iii) has been carried out but before process step ii) has been carried out.

The surface post-crosslinking of the water-absorbing polymer structure, in which the water-absorbing polymer structure is first brought into contact with a surface post-crosslinking agent and is then heated, is carried out in process step ii). In this context, the post-crosslinking agent is preferably brought into contact with the polymer particles in the form of a fluid $F_2$ comprising the post-crosslinking agent and a solvent, especially if it is not liquid under the post-crosslinking conditions. Solvents which are employed in this context are preferably water, water-miscible organic solvents, such as, for example, methanol, ethanol, 1-propanol, 2-propanol or 1-butanol, or mixtures of at least two of these solvents, water being most preferred as the solvent. It is furthermore preferable for the fluid $F_2$ to comprise the post-crosslinking agent in an amount in a range of from 5 to 75 wt. %, particularly preferably 10 to 50 wt. %, and most preferably 15 to 40 wt. %, based on the total weight of the fluid $F_2$.

In the process according to the invention, the water-absorbing polymer structure is preferably brought into contact with the fluid $F_2$ comprising the post-crosslinking agent by thorough mixing of the fluid $F_2$ with the water-absorbing polymer structure.

Suitable mixing units for application of the fluid $F_2$ are, for example, the Patterson-Kelley mixer, DRAIS turbulence mixer, Lodige mixer, Ruberg mixer, screw mixers, plate mixers and fluidized bed mixers as well as continuously operating vertical mixers, in which the polymer structure is mixed by means of rotating blades in rapid frequency (Schugi mixer). Mixing devices in which mixing of the fluid $F_2$ with the water-absorbing polymer structure is carried out at least partly in a rotating container can also be employed. Such mixing devices are obtainable, for example, from Lindor, Dordrecht, Holland and are marketed, for example, under the product names Lindor 70, Lindor 200, Lindor 500, Lindor 750, Lindor 1000, Lindor 1500, Lindor 2000, Lindor 2300, Lindor 4000, Lindor 7000, Lindor 8000, Lindor 12000, Lindor 14000 or Lindor 25000.

In the process according to the invention, during the post-crosslinking the water-absorbing polymer structure is preferably brought into contact with at most 20 wt. %, particularly preferably with at most 15 wt. %, moreover preferably with at most 10 wt. %, moreover still more preferably with at most 5 wt. % of solvent, preferably water, and most preferably of all with less than 3 wt. %, in each case based on the weight of the water-absorbing polymer structure.

In the case of polymer structures in the form of preferably spherical particles, it is furthermore preferable according to the invention for the components to be brought into contact in a manner such that merely the outer region, but not the inner region of the particulate water-absorbing polymer structures is brought into contact with the fluid $F_2$ and therefore the post-crosslinking agent.

Compounds which have at least two functional groups which can react with functional groups of a polymer structure in a condensation reaction (=condensation crosslinking agents), in an addition reaction or in a ring-opening reaction, or polyvalent metal cations which render possible a crosslinking of the polymer structure by means of electrostatic interaction between the polyvalent metal cation and the functional groups of a polymer structure are preferably understood as post-crosslinking agents which are employed in the process according to the invention. Preferred post-crosslinking agents in the process according to the invention are those which are mentioned as crosslinking agents of crosslinking agent classes II and IV in WO 2004/037903 A2.

Among these compounds, particularly preferred post-crosslinking agents are condensation crosslinking agents, such as, for example, diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

After the water-absorbing polymer structures have been brought into contact with the post-crosslinking agent or with the fluid comprising the post-crosslinking agent they are heated to a temperature in the range of from 50 to 300° C., preferably 75 to 275° C. and particularly preferably 150 to 250° C., so that, preferably as a result of this, the outer region of the polymer structures is more highly crosslinked compared with the inner region (=post-cross linking) The duration of the heat treatment is limited by the risk that the desired profile of properties of the water-absorbing polymer structures is destroyed as a result of the action of heat.

In process step iii) of the process according to the invention, the water-absorbing polymer structures are brought into contact a) with at least one tannin fraction which has a number-average molecular weight, determined in accordance with the test method described herein, of at least 1,000 g/mol, still more preferably of at least 1,100 g/mol and most preferably of at least 1,200 g/mol, or b) with at least one tannin fraction which has a weight-average molecular weight, determined in accordance with the test method described herein, of at least 1,000 g/mol, still more preferably of at least 1,100 g/mol and most preferably of at least 1,200 g/mol, or c) with at least one tannin fraction comprising hydrolysable gallotannins, preferred tannins being in particular those tannins which have already been mentioned above as preferred tannins in connection with the composition according to the invention. In particular, hydrolysable tannins, but especially hydrolysable gallotannins, are accordingly preferred. As already stated above, this bringing into contact with the tannins can be carried out before, during or after process step ii) has been carried out, it particularly preferably being carried out after process step ii).

According to a particularly preferred embodiment of the process according to the invention, tannins which are derived from the base skeleton of the following structure I (β-1,2,3,4,6-pentagalloyl-O-D-glucose)

structure I

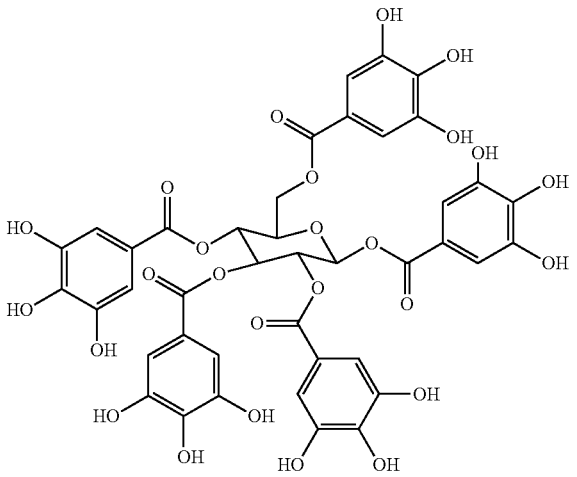

wherein to at least one of the OH groups of at least one of the gallic acid molecules bonded to the carbohydrate core (=gallic acid molecule of the first level, bonded as galloyl ester), preferably to one of the OH groups in the meta or para position, but preferably to at least one of the OH groups of 2, 3, 4 or 5 of the gallic acid molecules bonded to the carbohydrate core, there is bonded at least one further gallic acid molecule (=gallic acid molecule of the second level) via an ester bond (digalloyl ester), are employed. In this connection, it is particularly preferable for the tannin to be a tannin which is derived from the base skeleton of structure I and which includes at least one, preferably two, three, four or five gallic acid molecules of the second level. In particular, however, in this connection it is preferable for preferably at least 30 wt. %, particularly preferably at least 50 wt. %, still more preferably at least 75 wt. % and most preferably at least 95 wt. % of the tannins contained in the water-absorbing composition to have a molecular weight of more than 940 g/mol, particularly preferably more than 1,100 g/mol and moreover preferably more than 1,200 g/mol, here also preferably a molecular weight of 10,000 g/mol, particularly preferably of 5,000 g/mol not being exceeded.

It is furthermore particularly preferable in this context for the at least one tannin fraction to be employed in an amount in a range of from 0.001 to 10 wt. %, particularly preferably in a range of from 0.1 to 5 wt. % and most preferably in an amount in a range of from 0.2 to 2 wt. %, based on the total weight of the water-absorbing polymer structure. It his, however, particular advantageous in connection with the color stability of the water-absorbing composition after a contact with body liquids that the tannin or the tannin fraction is used in an amount of not more than 0.75 wt. %, particularly preferably not more than 0.5 wt. % and most preferably not more than 0.4 wt.-%, each based on the total weight of the water-absorbing polymer structures. According to a particular embodiment of the process for the preparation of a water-absorbing composition according to the present invention the tannin or the tannin fraction are used in an amount of 0.2 to 0.4 wt.-%, based on the total weight of the water-absorbing polymer structures.

According to a particularly preferred embodiment of the process according to the invention, the at least one tannin fraction is employed in process step ii) in the form of particles, in particular in the form of a powder, it being furthermore preferable in this connection for at least 50 wt. %, particularly preferably at least 75 wt. %, still more preferably at least 95 wt. % and most preferably 100 wt. % of the particles of the at least one tannin fraction to have a size in a range of from 10 nm to 300 μm, particularly preferably 50 nm to 50 μm and most preferably 100 nm to 10 μm.

It is furthermore preferable in particular in connection with the use of the at least one tannin fraction in the form of particles for the at least one tannin fraction to have at least one of the following properties:

A) a density in a range of from 0.2 to 0.6 g/cm$^3$, particularly preferably in a range of from 0.3 to 0.45 g/cm$^3$;

B) a pH as a 1 wt. % solution in water at 20° C. in a range of from 2 to 5, particularly preferably in a range of 2.5-4;

C) a content of free gallic acid of less than 0.5 wt. %, particularly preferably less than 0.1 wt. %, in each case based on the total weight of the tannin fraction;

D) a purity, stated as the tannin content, of at least 90 wt. %, particularly preferably at least 95 wt. %, in each case based on the total weight of the tannin fraction.

Embodiments of the tannin fraction which can preferably be employed in the process according to the invention which are furthermore preferred have any conceivable combination of the above features A to D, the embodiments of the following combinations of features being preferred: A, B, C, D, AB, AC, AD, BC, BD, CD, ABC, ABD, ACD, BCD and ABCD.

The tannin fraction which can be employed in the process according to the invention can be isolated from a suitable plant source or obtained from commercial suppliers, as has already been described above in connection with the composition according to the invention.

The water-absorbing polymer structures optionally already post-crosslinked on the surface are preferably brought into contact with the at least one tannin fraction by simple mixing of the two components, the at least one tannin fraction preferably being mixed in particulate form with the water-absorbing polymer structure. However, it is also conceivable in principle for the tannin fraction to be mixed with the water-absorbing polymer structure in the form of a solution or a suspension, for example in the form of an aqueous solution. As already stated above, however, the mixing of the at least one tannin fraction in particulate form, in particular in the form of a powder, with the water-absorbing polymer structures has proved to be advantageous in particular.

Suitable mixing units for mixing of the at least one tannin fraction and the water-absorbing polymer structures are, for example, the Patterson-Kelley mixer, DRAIS turbulence mixer, Lodige mixer, Ruberg mixer, screw mixers, plate mixers and fluidized bed mixers as well as continuously operating vertical mixers, in which the polymer structure is mixed by means of rotating blades in rapid frequency (Schugi mixer). Here also, the use, already described in connection with the surface post-crosslinking, of mixing devices in which the mixing of the pulverulent tannins or of the tannin solutions with the water-absorbing polymer structures is carried out at least partly in a rotating container is conceivable.

According to a preferred embodiment of the process according to the present invention this process comprises the further process step iv) of bringing the water-absorbing polymer structures into contact with one or more complex forming agents, wherein process step iv), in the same way as process step iii), can be carried out before, during or after process step ii), but is preferably carried out after process step ii) (which means that water-absorbing polymer structures which have already been post-crosslinked on the surface are brought into contact with the corresponding complex forming agents). With respect to the use of the tannin fraction, it is basically possible

- to first bring into contact the tannin fraction with the water-absorbing polymer structures and then to add the complex forming agent;
- to first bring into contact the complex forming agent with the water-absorbing polymer structures and then to add the complex forming agent;
- to bring into contact the complex forming agent with the water-absorbing polymer structures together with the tannin fraction.

As complex forming agents are those complex forming agents preferred that have already been mentioned above in connection in connection with the water-absorbing composition according to the present invention as preferred complex forming agents. It is furthermore preferred according to the present invention that the complex forming agents is used in an amount in the range from 0.001 to 5 wt.-%, particular preferably in the range from 0.01 to 1 wt.-% and most preferably in the range from 0.05 to 0.5 wt. %, each based on the total weight of the water-absorbing polymer structure.

The bringing into contact of the water-absorbing polymer structure with the tannin fraction and the complex forming agent can be performed in different ways. According to a preferred embodiment of the process according to the present invention the tannin fraction is dry mixed with the water-absorbing polymer structure in the form of particles and the complex forming agent is used in the form of an aqueous solution. In this manner dust formation in the absorbent composition resulting from the dryly added tannin can be significantly reduced. It is, however, also conceivable to bring into contact an aqueous solution comprising the tannin fraction and the complex forming agent with the water-absorbing polymer structure. In this context it is preferred that such an aqueous solution contains the tannin fraction in a concentration in the range from 5 to 50 wt. %, particular preferably 7.5 to 30 wt.-% and most preferably 10 to 20 wt.-%, based on the total weight of the aqueous solution, wherein it is particular advantageous to select the concentration such that it is lower or equal to 20 wt.-% since this leads to a particularly homogeneous distribution of the tannin fraction on the surface of the water-absorbing polymer structure. The concentration of the complex forming agent in the aqueous solution is preferably in the range from 20 to 60 wt. %, particular preferably in the range from 30 to 50 wt. %, each based on the total weight of the aqueous solution. Besides the addition of an aqueous solution commonly containing the tannin fraction and the complex forming agent it is also possible to add separate solutions (i.e. one aqueous solution containing the complex forming agent and one aqueous solution containing the tannin fraction), wherein it is preferred in this context that the tannin concentration and the concentration of the complex forming agent in the respective aqueous solution is lying within the concentration ranges previously mentioned with respect to the common aqueous solution. The term "aqueous solution" as used herein comprises any solution in which the solvent or the solvent mixture is based to at least 50 wt.-%, particular preferably to at least 75 wt.-% and most preferably to at least 90 wt.-%, each based on the total weight of the solvent, on water.

The addition of the separately added aqueous solutions, of the common aqueous solution or the dry mixed tannin fraction and the aqueous solution of the complex forming agent can again be preformed in suitable mixing units, such as the Patterson-Kelley mixer, DRAIS turbulence mixer, Lodige mixer, Ruberg mixer, screw mixers, plate mixers and fluidized bed mixers as well as continuously operating vertical mixers, in which the polymer structure is mixed by means of rotating blades in rapid frequency (Schugi mixer). For this purpose it is also possible to use mixing devices in which the mixing of the water-absorbing polymer structures with the dryly added components or the aqueous solutions is carried out at least partly in a rotating container is conceivable.

In connection with the use of complex forming agent it corresponds to a particular embodiment of the process for the preparation of a water-absorbing composition according to the present invention that this process comprises the process steps:

i) provision of a water-absorbing polymer structure;

ii) post-crosslinking of the water-absorbing polymer structure;

iii) bringing the water-absorbing polymer structure into contact with at least one tannin fraction comprising a tannin, wherein it is preferred that this tannin fraction is one of the above mentioned tannin fractions (a tannin fraction having a weight-average molecular weight, determined in accordance with the test method described herein, of at least 1,000 g/mol, a tannin fraction having a number-average molecular weight, determined in accordance with the test method described herein, of at least 1,000 g/mol or a tannin fraction comprising hydrolysable tannins), and wherein in this case the tannin fraction can be used in a purified form or in the form of a plant extract, particularly in the form of a tee extract;

iv) bringing the water-absorbing polymer structures into contact with one or more complex forming agents;

wherein process steps iii) and iv) can be carried out before, during or after process step ii), but is preferably carried out after process step ii) (which means that water-absorbing polymer structures which have already been post-crosslinked on the surface are brought into contact with the corresponding tannin and the complex forming agent).

After the water-absorbing polymer structures have been brought into contact with the at least one tannin fraction and optionally with the at least one complex forming agent, the composition obtained in this way can be subjected to still further modification measures. The addition of the binders mentioned above in connection with the composition according to the invention is conceivable here in particular.

A contribution towards achieving the abovementioned objects is also made by a water-absorbing composition which is obtainable by the process according to the invention described above.

It is particularly preferable for the composition according to the invention described above and also the composition according to the invention obtainable by the process described above to have at least one of the following properties:

(β1) a retention, determined in accordance with ERT 441.2-02, of at least 20 g/g, preferably at least 25 g/g and particularly preferably in a range of from 25 to 50 g/g;

(β2) an absorption, determined in accordance with ERT 442.2-02, (in the case of particles for the total particle size fraction) against a pressure of 0.7 psi (50 g/cm$^2$) of at least 15 g/g, particularly preferably of at least 20 g/g;

(β3) a degree of neutralization of at most 78 mol %, particularly preferably of at most 70 mol % and at least 50 mol %.

A contribution towards achieving the abovementioned objects is also made by a composite comprising a water-absorbing composition according to the invention or a water-absorbing composition which is obtainable by the process according to the invention and a substrate.

In this context it is preferable for the water-absorbing composition according to the invention and the substrate to be firmly bonded to one another. Preferred substrates are films of polymers, such as, for example, of polyethylene, polypropylene or polyamide, metals, nonwovens, fluff, tissues, woven fabric, natural or synthetic fibers or other foams. It is furthermore preferable according to the invention for the composite to comprise at least one region which comprises the water-absorbing composition according to the invention in an amount in a range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the region in question in the composite, this region preferably having a size of at least 0.01 $cm^3$, preferably at least 0.1 $cm^3$ and most preferably at least 0.5 $cm^3$.

In one embodiment of the composite according to the invention, the composite is a flat composite such as is described as "absorbent material" in WO 02/056812 A1. The disclosure content of WO 02/056812 A1, in particular with respect to the exact structure of the composite, the weight of its constituents per unit area and its thickness, is introduced herewith as reference and represents a part of the disclosure of the present invention.

A further contribution towards achieving the abovementioned objects is also made by a process for the production of a composite, wherein the water-absorbing composition according to the invention or the water-absorbing composition obtainable by the process according to the invention and a substrate and optionally an additive are brought into contact with one another. Substrates which are preferably employed are those substrates which have already been mentioned above in connection with the composite according to the invention.

A contribution towards achieving the abovementioned objects is also made by a composite obtainable by the process described above, this composite preferably having the same properties as the composite according to the invention described above.

According to another aspect of the present invention, the composite is constructed as a hygiene article core which comprises, in each case based on the hygiene article core, at least 30 wt. %, preferably at least 50 wt. % and moreover preferably at least 70 wt. % of the water-absorbing composition according to the invention and at least 1 wt. %, preferably at least 5 wt. % and moreover preferably at least 10 wt. % of the substrate and optionally also further conventional auxiliaries and/or adhesives, wherein the sum of the percentages by weight of the individual components contained in the hygiene article core gives 100 wt. %. Materials which serve to fix the superabsorbent composition according to the invention, which is usually in the form of particles, are particularly preferred as the substrate in connection with the hygiene article core. These can be fibers or knitted fabrics or woven fabrics as well as nets. It is furthermore possible for the water-absorbing composition, which, for example, is in the form of a powder and therefore particulate, to be bonded to the substrate by an adhesive, such as a glue. The substrate being configured such that the water-absorbing composition is accommodated in a recess of the substrate likewise corresponds to an embodiment. Conventional auxiliaries which can likewise be incorporated into the hygiene article core are, for example, cosmetic substances, substances which increase skin tolerability, disinfectants, antimicrobial substances and the like.

In a further aspect, the present invention relates to hygiene articles comprising an upper layer which is permeable to liquid, a lower layer which is impermeable to liquid and a composite according to the invention arranged between the upper layer and the lower layer. Possible hygiene articles are both feminine hygiene articles and adult incontinence products, and nappies for infants, babies and small children. It is preferable for the hygiene article to comprise a hygiene article core described above. All those woven fabrics, laid fabrics and knitted layers, which are usually made of celluloses or cellulose derivatives and are optionally bonded with plastics, such as polypropylene or polyethylene, which are known and seem suitable to the person skilled in the art for this purpose are in principle possible as the upper layer which is permeable to liquid. The nonwovens which are usually likewise made of a cellulose or cellulose derivative laid fabric, knitted fabric or stitched fabric and which are familiar to the person skilled in the art in the industry are also employed as the lower layer which is impermeable to liquid, these nonwovens in general being sealed with a layer of plastic, usually of polypropylene or polyethylene.

A further contribution towards achieving the abovementioned objects is made by chemical products comprising the water-absorbing compositions according to the invention or a composite according to the invention. Preferred chemical products are, in particular, foams, shaped articles, fibers, foils, films, cables, sealing materials, liquid-absorbing hygiene articles, in particular nappies and sanitary towels, carriers for plant or fungal growth-regulating agents or plant protection active compounds, additives for building materials, packaging materials or soil additives.

The use of the water-absorbing composition according to the invention or of the composite according to the invention in chemical products, preferably in the above-mentioned chemical products, in particular in hygiene articles, such as nappies or sanitary towels, and the use of the superabsorber particles as carriers for plant or fungal growth-regulating agents or plant protection active compounds also make a contribution towards achieving the abovementioned objects. For the use as a carrier for plant or fungal growth-regulating agents or plant protection active compounds it is preferable for it to be possible for the plant or fungal growth-regulating agents or plant protection active compounds to be released over a period of time controlled by the carrier.

A contribution towards achieving the abovementioned objects is furthermore made by the use of

- a tannin fraction which has a number-average molecular weight, determined in accordance with the test method described herein, of at least 1,000 g/mol, still more preferably of at least 1,100 g/mol and most preferably of at least 1,200 g/mol, or
- a tannin fraction which has a number-average molecular weight, determined in accordance with the test method described herein, of at least 1,000 g/mol, still more preferably of at least 1,100 g/mol and most preferably of at least 1,200 g/mol, or
- hydrolysable gallotannins for improving the odor-binding properties of water-absorbing polymer structures, those tannins and water-absorbing polymer structures which have already been mentioned above as preferred tannins and as preferred water-absorbing polymer structures in connection with the water-absorbing composition according to the invention being particularly preferred as tannins and as water-absorbing polymer structures. According to a particular preferred embodiment of the use according to the present invention the tannin fraction is used in combination with a complex forming agent, wherein as complex forming agents those complex forming agents are preferred that have already been mentioned previously in connection with the water-absorbing composition as preferred complex forming agents. According to a further particular preferred embodiment of the use according to the present invention this use relates to the use of a tannin fraction comprising a tannin, preferably a tannin fraction with the previously mentioned weight- or number-average molecular weight or a tannin fraction comprising a hydrolysable gallotannin, in combination with one or more complex forming agents for improving the odor-binding properties of water-absorbing polymer structures.

The invention is explained in detail below with the aid of test methods and non-limiting figures and examples.

FIG. 1 shows the odor-binding effect of the use according to the invention of tannins with superabsorbers having a varying degree of neutralization.

Figure 2:
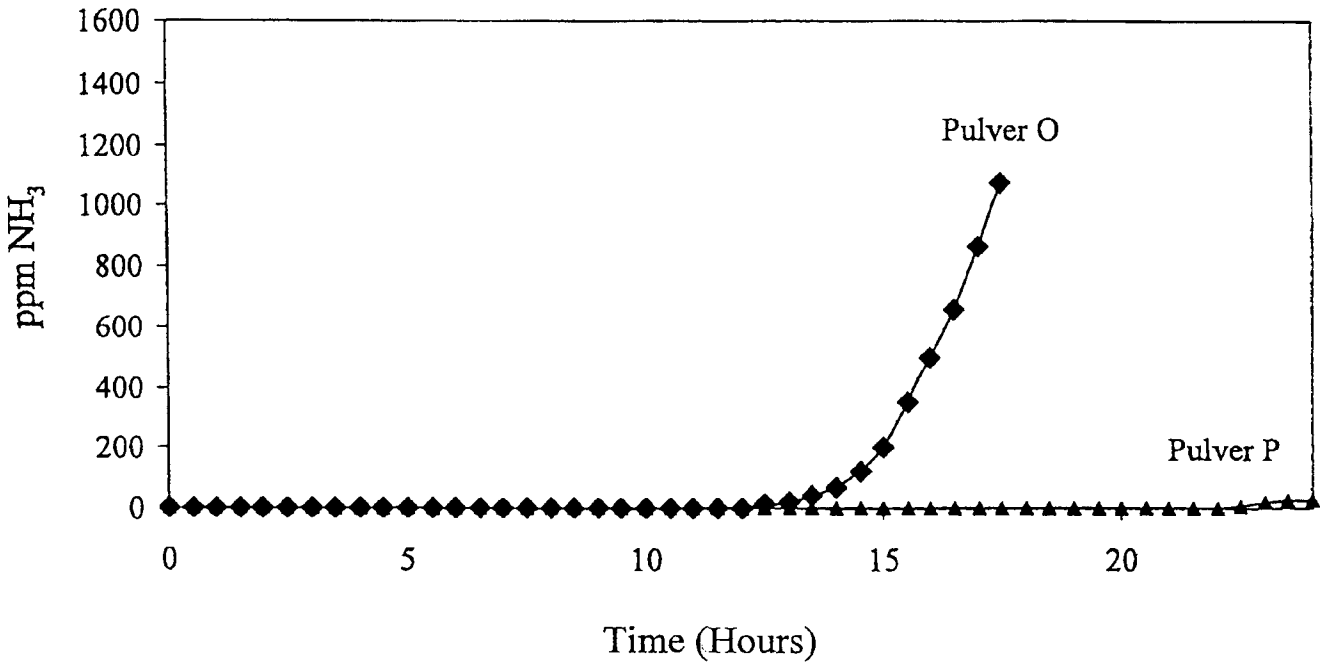
FIG. 2 is another graph showing a comparison of ppm of $NH_3$ and time in hours.

FIG. 2 shows the odor-binding effect of the combined use according to the invention of tannins and complex forming agents.

Test Methods

General

Unless other test methods are given in the following, the test methods which are generally known to the person skilled in the art and appear to be conventional are used, test methods of EDANA (European Diaper and Nonwoven Association), which are generally given as "ERT methods", being used in particular.

Determination of the Molecular Weight and the Polydispersity of the Tannins

The determination of the weight-average and also of the number-average molecular weight and of the polydispersity of the tannins, in particular of the hydrolysable tannins which are preferably to be employed according to the invention, is preferably carried out via a MALDI-TOF MS analysis such as is described, for example, by C. Mane et al., "Assessment of the Molecular Weight Distribution of Tannin Fractions through MALDI-TOF MS Analysis of Protein-Tannin Complexes", Analytical Chemistry, vol. 79 (6), pages 2239 to 2248 (2007).

Determination of the Molecular Weight of Gallotannins

The molecular weight of gallotannins can also be determined by so-called "straight phase" HPLC methods, in addition to the test method described above. In this method, two different mobile phases (mobile phase A: n-hexane; mobile phase B: 750 ml of methanol, 250 ml of THF and 2.5 g of citric acid) are combined with one another in different relative amounts with respect to time. The sequence of combination of mobile phases A and B with respect to time was chosen as follows:

| Time [min] | Mobile phase A [%] | Mobile phase B [%] |
|---|---|---|
| 0.00 | 80 | 20 |
| 15.00 | 50 | 50 |
| 30.00 | 35 | 65 |
| 31.00 | 20 | 80 |
| 35.00 | 0 | 100 |
| 40.00 | 0 | 100 |
| 41.00 | 80 | 20 |
| 45.01 | 80 | 20 |

The following apparatuses and materials are employed:

HPLC pump system 325 from KONTRON Instruments

DEGASYS DG-1300 UniFlows

HPLC autosampler 465 BIO-TEK Systems

HPLC detector 430 from KONTRON Instruments

KromaSystem 2000 software

LichroCart 250-4, LichroSorb Si60 Merck 1.51351.0001#

Column: LiChrosorb SI 60 Merck 1.51351.0001 LiChroCART 250-4 OB281194

For carrying out the chromatography, 100 mg of the gallotannin sample to be analyzed are dissolved in methanol in a 100 ml volumetric flask. The sample is injected into the HPLC device. The following parameters are maintained:

Flow rate: 2 ml/min

Wavelength: 280 nm

Range: 0-500

Column oven: 35° C.

Pure commercially obtainable β-1,2,3,4,6-pentagalloyll-O-D-glucose is employed as the standard.

Determination of the L,a,b-Color Values

The determination of the L,a,b-color values occurs by means of a spectral colorimeter "Hunter LabScan XE" (Hunter Associates Laboratory, Reston, Va., USA) with the following setting:

| | |
|---|---|
| "Mode" | 0/45 |
| "Area View" | 44.5 mm |
| "Port Size" | 50.8 mm |
| "UV-Filter" | nominal |

Before each measurement, the LabScan XE is calibrated, in that first the black glass plate belonging to the device accessories is clamped between sample plate and measurement opening, whereby the glass plate is placed on a petri dish (diameter 100 mm, depth: 15 mm) and the calibration with the black glass plate started by activation of the "OK"-switch. Subsequently, in the same way, the white standard plate is laid on the petri dish and the calibration carried by activation of the "OK"-switch.

After the calibration has been carried out, the "Read Std"-switch is pressed, in order to check the function capability of the measurement device, whereby the standard plate is not yet removed. Subsequently, the "Read"-switch is activated for measurement of the L,a,b-value for the standard plate. The standard plate is then removed.

For the measurement 3 g of the water-absorbing composition which is to be measured was finely distributed on the bottom of a petri dish. 90 g of a $FeCl_2$-solution having a $FeCl_2$-concentration of 0.0033% in 0.9% NaCl-solution was added gradually and homogenized. After an equal swelling and coloration has occurred, the overflowing gel has been wiped of and the sample is measured immediately in the Hunter color device in order to avoid that the gel is ripped of after drying. To achieve a better differentiation, a white paper was placed under each petri dish. Using this white paper, the following control values were obtained: L=96.97; a=4.02; b=−21.68.

EXAMPLES

Example 1a

Provision of a Water-Absorbing Polymer Structure (Process Step i))

A monomer solution comprising 300 g of acrylic acid, which was neutralized to the extent of 70 mol % with sodium hydroxide solution, 441 g of water, 0.9 g of polyethylene glycol 300 diacrylate and 1.35 g of allyloxypolyethylene glycol acrylate is freed from dissolved oxygen by flushing with nitrogen and cooled to the start temperature of 4° C. When the start temperature was reached, the initiator solution (0.3 g of sodium peroxydisulphate in 10 g of $H_2O$, 0.07 g of 35% hydrogen peroxide solution in 10 g of $H_2O$ and $H_2O$ and 0.015 g of ascorbic acid in 2 g of $H_2O$) was added. When the end temperature of approx. 100° C. was reached, the gel formed was chopped such that granules with particles of about 1 to 3 mm in size were obtained. The water content was approx. 50%. These particles were dried at 150° C. for 120 minutes. The dried polymer was crushed coarsely, ground and sieved to a powder having a particle size of from 150 to 850 μm, and a water-absorbing polymer structure (powder A) having an average particle size according to ERT 420.2-02 of 520 μm was obtained. The water content, determined in accordance with ERT 430.1-99, was 5%.

Example 2a

Surface Post-Crosslinking of a Water-Absorbing Polymer Structure (Process Step ii))

For the post-crosslinking, 100 g of powder A obtained above were mixed with a solution of 1 g of 1,3-dioxolan-2-one and 3 g of water, with vigorous stirring, and the mixture was then heated for 30 minutes in an oven temperature-controlled at 180° C. The water-absorbing polymer structure post-crosslinked on the surface obtained in this way (powder B) had an average particle size according to ERT 420.2-02 of 525 μm. The water content determined in powder B in accordance with ERT 430.1-99 was 4.5%.

Example 1b

Provision of a Water-Absorbing Polymer Structure (Process Step i))

A monomer solution comprising 300 g of acrylic acid, which was neutralized to the extent of 55 mol % with sodium hydroxide solution, 491 g of water 0.9 g of polyethylene glycol 300 diacrylate and 1.35 g of allyloxypolyethylene glycol acrylate is freed from dissolved oxygen by flushing with nitrogen and cooled to the start temperature of 4° C. When the start temperature was reached, the initiator solution (0.3 g of sodium peroxydisulphate in 10 g of $H_2O$, 0.07 g of 35% hydrogen peroxide solution in 10 g of $H_2O$ and 0.015 g of ascorbic acid in 2 g of $H_2O$) was added. When the end temperature of approx. 100° C. was reached, the gel formed was chopped such that granules with particles of about 1 to 3 mm in size were obtained. The water content was approx. 50%. These particles were dried at 150° C. for 120 minutes. The dried polymer was crushed coarsely, ground and sieved to a powder having a particle size of from 150 to 850 μm, and a water-absorbing polymer structure (powder C) having an average particle size according to ERT 420.2-02 of 520 μm was obtained. The water content, determined in accordance with ERT 430.1-99, was 5%.

Example 2b

Surface Post-Crosslinking of a Water-Absorbing Polymer Structure (Process Step ii))

For the post-crosslinking, 100 g of powder C obtained above were mixed with a solution of 1 g of 1,3-dioxolan-2-one and 3 g of water, with vigorous stirring, and the mixture was then heated for 30 minutes in an oven temperature-controlled at 180° C. The water-absorbing polymer structure post-crosslinked on the surface obtained in this way (powder D) had an average particle size according to ERT 420.2-02 of 525 μm. The water content determined in powder D in accordance with ERT 430.1-99 was 4.5%.

Example 3

Bringing a Water-Absorbing Polymer Structure into Contact with Tannins (Process Step iii))

The water-absorbing polymer structure post-crosslinked on the surface obtained in Example 2a (powder B) was mixed with various particulate hydrolysable gallotannins (see the data in the following Tables 1 and 2). The compositions according to the invention according to powders E to G and H to J were thereby obtained:

TABLE 1

| | Powder B (comparison) | Powder E | Powder F | Powder G |
|---|---|---|---|---|
| Tannin | Floctan ® 1 | Floctan ® 1 | Floctan ® 1 | Floctan ® 1 |
| Amount [wt. %] | 0 | 0.5 | 0.75 | 1.0 |
| TB [g/g] | 30.0 | 29.0 | 29.0 | 29.0 |
| $AAP_{0.7psi}$ [g/g] | 21.1 | 18.6 | 18.9 | 18.4 |

TABLE 2

| | Powder B (comparison) | Powder H | Powder I | Powder J |
|---|---|---|---|---|
| Tannin | Brewtan ® | Brewtan ® | Brewtan ® | Brewtan ® |
| Amount [wt. %] | 0 | 0.5 | 0.75 | 1.0 |
| TB [g/g] | 30.0 | 29.7 | 28.0 | 28.1 |
| $AAP_{0.7psi}$ [g/g] | 21.1 | 20.0 | 19.5 | 18.5 |

It can be seen from the results of Tables 1 and 2 that the addition according to the invention of the hydrolysable tannins scarcely noticeably influences the absorption properties of the water-absorbing polymer structures.

Example 4

Determination of the Odor-Binding Properties of the Compositions According to the Invention In a further experiment, powders B and D were mixed again with 0.5 wt. % of Floctan® 1, 1,000 ppm of polyethylene glycol (molecular weight=10,000 g/mol), applied in the form of a 4.6 wt. % solution, additionally being added. Powders K (starting from powder B, 70% neutralized) and L (starting from powder D, 55% neutralized) were thereby obtained.

The odor-binding properties of powders B, D, K and L were determined.

The odor-binding properties of the compositions according to the invention were determined via determination of the release of ammonia by the water-absorbing composition.

For this, Proteus mirabilis cells were cultured overnight on CASO slant agar at 37° C. Each tube was washed off with 5 ml of synthetic urine. The bacteria suspension was adjusted to a germ content of approximately $10^5$ CFU/ml (CFU=colony-forming units) with synthetic urine and 1 g/l of meat extract and 1 g/l of peptone.

33 ml of the synthetic urine which contained 1 g/l of meat extract and 1 g/l of peptone and to which bacteria had been added were added to 1 g portions of the water-absorbing composition. On the one hand a batch without a composition according to the invention and a water-absorbing composition without tannins was employed as a control.

The vessels were closed with a rubber stopper, through the bore of which a Dräger diffusion tube was led, and incubated in an incubating cabinet at 37° C. The ammonia released was measured in ppm×h. The initial germ count (measured in CFU) of the urine was determined by plating out suitable dilutions on nutrient media plates. For the release of ammonia, the mean of two batches was calculated.

The odor-binding properties of powders B, D, K and L according to the invention can be seen in FIG. 1. It can be seen from this figure that the combination of a water-absorbing polymer structure partly neutralized to the extent of only 55 mol % with hydrolysable tannins leads in particular to products having particularly advantageous odor-binding properties.

Example 5

Use of the Tannins in the Form of Aqueous Solutions

Example 3 is repeated, the tannins being applied not in powder form but in the form of an approximately 30 wt. % aqueous solution to powders B and D. The absorption properties of powders M (starting from powder B, 70% neutralized) and N (starting from powder D, 55% neutralized) obtained in this way are shown in the following Table 3.

TABLE 3

| | Powder M | Powder N |
|---|---|---|
| Tannin | Floctan ® 1 | Floctan ® 1 |
| Amount of tannin, based on the polymer [wt. %] | 0.5 | 0.5 |
| Amount of tannin solution employed, based on 100 g of polymer [g] | 1.7 | 1.7 |
| TB [g/g] | 34.0 | 30.0 |
| $AAP_{0.7psi}$ [g/g] | 20.2 | 19.4 |

It can be seen from Table 3 that the tannins can also be employed in the form of aqueous solutions.

Example 6

Combined Use of Tannins and Complex Forming Agents

In a further experiment powder B was again mixed with 0.5 wt. % of Floctan®1, whereby additionally 1,000 ppm polyethylene glycol (molecular weight=10,000 g/mol), applied in the form of a 4.6 wt. % solution, were added. Powder O was thereby obtained.

In a further experiment powder B was mixed with 0.5 wt. % of Floctan 1 as well as with 0.1 wt.-% Versenex® (pentasodium salt of diethylenetriamine pentaacetic acid, applied in the form of a 40 wt.-% aqueous solution). Powder P was thereby obtained.

The odor-binding properties of powders O and P were determined according to the procedure described in Example 4. The result is shown in FIG. 2. There it can be seen that by using a complex forming agent (Versenex®) the odor-binding properties of superabsorbents that are treated with tannins can still be significantly improved.

Example 7

Combined Use of Tannins and Complex Forming Agents

In a further experiment powder B was again dry mixed with 0.5 wt. % of Floctan®1. Powder Q was thereby obtained.

In a further experiment powder B was mixed with 0.5 wt. % of Floctan 1 as well as with increasing amounts of Versenex® (0.1 wt.-%, 0.5 wt.-% and 0.75 wt.-%), applied in each case in the form of a 40 wt.-% aqueous solution). Powders R, S and T were thereby obtained.

From powders Q, R, S and T the color values were determined according to the L,a,b-color system after these polymers have been swollen with $Fe^{2+}$-containing solution, as described in connection with the previously described test methods. The following values have been determined:

TABLE 4

| Powder | L | a | b |
|---|---|---|---|
| Q | 15.88 | 2.72 | −0.98 |
| R | 27.67 | 7.00 | 1.31 |
| S | 37.44 | 7.54 | 6.30 |
| T | 55.37 | 1.59 | 8.11 |

As can be seen from table 4, the combined use of tannins and complex forming agents leads to a significantly improved color stability of the water-absorbing composition when this composition is brought into contact with $Fe^{2+}$-containing solutions, such as menstruation liquid.

The invention claimed is:

1. A water-absorbing composition comprising a) surface crosslinked water-absorbing polymer structures having a surface, wherein the water-absorbing polymer structures are based on partly neutralized, crosslinked polyacrylates; *and* b) from about 0.01 to 1 wt. %, based on the total weight of the water-absorbing composition, of a hydrolysable gallotannin located on the surface of the surface crosslinked water-absorbing polymer structures, wherein said hydrolysable gallotannin has a number-average molecular weight of at least 1,000 g/mol or a weight-average molecular weight of at least 1,000 g/mol; wherein said hydrolysable gallotannin is derived from β-1,2,3,4,6-pentagalloyl-O-D-glucose; wherein to at least one of the OH groups of at least one of the gallic acid molecules bonded to the carbohydrate core there is bonded a further gallic acid molecule via an ester bond; wherein at least 30 wt. % of the tannins contained in the water-absorbing composition have an average molecular weight of more than about 940 g/mol; and wherein said hydrolysable gallotannin is at least partially in the form of particles on the surface of the water-absorbing polymer structures; [and c) from about 0.01 to about 1 wt. %, based on the total weight of the water-absorbing polymer structures, of a complex forming agent located on the surface of the surface crosslinked water-absorbing polymer structures, wherein said complex forming agent comprises two or more functional groups selected from the group consisting of organic acid groups, amine or imine groups, and sulfonic acid groups,]

wherein the water-absorbing composition has at least one of the following properties:

(β1) a retention, determined in accordance with ERT 441.2-02, of at least 20 g/g;

(β2) an absorption, determined in accordance with ERT 442.-2-02, [(in the case of particles for the total particle size fraction)] against a pressure of 0.7 psi [(50 g/cm$^2$)] of at least 15 g/g; and (β3) a degree of neutralization of the polyacrylates of at least 50 mol % and at most 70 mol %.

2. The water-absorbing composition according to claim 1, wherein the hydrolysable gallotannin has a polydispersity of less than 5.

3. The water-absorbing composition according to claim 1, wherein the water-absorbing polymer structures have an inner region and an outer region surrounding the inner region, the outer region having a higher degree of cross-linking than the inner region.

4. The water-absorbing composition according to claim 1, wherein at least 50 wt. % of the particles of the hydrolysable gallotannin have a size in a range of from about 10 nm to about 300 μm.

5. The water-absorbing composition according to claim 1, wherein the particles of the hydrolysable gallotannin are immobilized on the surface of the water-absorbing polymer structures via a binder.

6. The water-absorbing composition according to claim 1, wherein the hydrolysable gallotannin is based on tannins which have been purified from a plant extract chosen from the group consisting of Rhus semialata extract, Rhus coriaria extract, Quercus infectoria extract, Quercus aegilops extract, Caesalpina spinosa extract, Caesalpina d. gyna extract, Valonea extract, chestnut wood extract and Terminalia chebula extract or a mixture of at least two of these.

7. The water-absorbing composition according to claim 1, [wherein the complex forming agent is an aminopolycarboxylic acid] *further comprising c) from about 0.01 to about 1 wt. %, based on the total weight of the water-absorbing polymer structures, of a complex forming agent located on the surface of the surface crosslinked water-absorbing polymer structures, wherein said complex forming agent comprises two or more functional groups selected from the group consisting of organic acid groups, amine or imine groups, and sulfonic acid groups*.

* * * * *